United States Patent [19]

Sherman-Gold

[11] Patent Number: 5,792,799
[45] Date of Patent: Aug. 11, 1998

[54] PARENTERAL DELIVERY OF MAO A INHIBITORS

[75] Inventor: Rivka Sherman-Gold, Palo Alto, Calif.

[73] Assignee: Athena Neurosciences, Inc., South San Francisco, Calif.

[21] Appl. No.: 729,290

[22] Filed: Oct. 10, 1996

[51] Int. Cl.$^6$ ................................................. A61K 31/135
[52] U.S. Cl. ...................... 514/651; 514/647; 514/654; 514/655
[58] Field of Search ................................ 514/651, 650, 514/649, 643, 647, 654, 655

[56] References Cited

PUBLICATIONS

Folks, D.G., "Monoamine Oxidase Inhibitors: Reappraisal of Dietary Considerations", *J. of Clinical Psychopharmacology*, 3:249–252 (1983).

Blackwell, B., et al., "Interaction Between Cheese and Monoamine–Oxidase Inhibitors in Rats and Cats" *Lancet*, 1:530–531 (1964).

Kato, T., et al., "Brain Dialysis: In Vivo Metabolism of Dopamine and Serotonin by Monoamine Oxidase A but Not B in the Striatum of Unrestrained Rats", *J. of Neurochemistry*, 46:1277–1282 (1986).

Riederer, P., et al., "Monoamine Oxidase Activity and Monoamine metabolism in Brains of Parkinsonian Patients Treated with 1–Deprenyl" *J. of Neurochemistry*, 46:1359–1365 (1986).

Butcher, S.P., et al., "Effects of Selective Monoamine Oxidase Inhibitors on the In Vivo Release and Metabolism of Dopamine in the Rat Striatum", *J. of Neurochemistry*, 55:981–988 (1990).

Parkinson Study Group, Effect of Deprenyl on the Progression of Disability in Early Parkinson's Disease, *N. Engl. J. Med.*, 321:1364–1371 (1989).

Yu, P.H., et al., "Differential Expression of Type A and Type B Monoamine Oxidase of Mouse Astrocytes in primary Cultures", *J. of Neurochemistry*, 39:1492–1495 (1982).

Aulakh et al., Pharmacol., Biochem. Behav., 55(2), 265–8 (1996).

Brannan et al., J. Neural Trausm.: Parkinson's Dis. Dementia Sect., 10(2–3), 79–89 (1995).

*Primary Examiner*—Phyllis G. Spivak
*Attorney, Agent, or Firm*—Hamilton, Brook, Sith & Reynolds, P.C.

[57] ABSTRACT

Methods of treating Parkinson's disease in a human by administering an effective amount of at least one monoamine oxidase (MAO) A inhibitor by a nasal, intrapulmonary or parenteral routes are disclosed. Reversible or irreversible MAO A inhibitors, or non-selective MAO inhibitors, can be used, and more than one MAO A inhibitor can be administered concurrently. The MAO A inhibitor can be administered in conjunction with other drugs, such as MAO B inhibitors.

13 Claims, 10 Drawing Sheets

PARENTERAL DELIVERY OF MAO A INHIBITORS

BACKGROUND OF THE INVENTION

Parkinson's disease is a chronic, progressive neurological disorder characterized by bradykinesia (slowness or poverty of movement), muscular rigidity, tremors and weakness of resting muscles, and abnormalities of posture and gait. Emotions may be affected and mental capacity may also be impaired. The disease is caused by deficiency in dopaminergic innervation, due to degeneration of neurons in the substantia nigra. In the majority of Parkinson's disease cases, there is no known cause. Parkinson's disease usually appears after age 40.

The discovery that the monoamine oxidase (MAO) B inhibitor deprenyl possesses beneficial symptomatic effects and possibly slows the progression of Parkinson's disease has emphasized the potential therapeutic relevance of MAO inhibitors (Parkinson Study Group, N. Engl. J. Med. 321:1364–1371 (1989)). However, several investigators have suggested that MAO A inhibitors may be even more effective than deprenyl in relieving symptoms as well as counteracting the process of neurodegeneration, since experimental evidence indicates that an important mechanism for dopamine catabolism occurs via reuptake of the neurotransmitter into dopaminergic nerve terminals, where it is deaminated by MAO A (Paterson et al., J. Pharmacol. Exp. Ther. 258:1019–1026 (1991)). The use of MAO A inhibitors as therapeutic agents in Parkinson's disease and other diseases has been hampered, however, by the significant peripheral side effects of these drugs. In particular, inhibition of MAO A in the gut is thought to be responsible for hypertensive crisis following ingestion of foods containing high levels of tryamine, such as cheese and red wine (the "cheese effect"). Before MAO A inhibitors can be used as therapeutic agents in Parkinson's disease and other diseases, a means to control the unwanted side effects of MAO A inhibitors, particularly the "cheese effect," is necessary.

SUMMARY OF THE INVENTION

The invention pertains to the discovery that parenteral administration of a MAO A inhibitor profoundly inhibits MAO A activity in the brain, while maintaining significant MAO A activity in the intestine. As a result of this discovery, there are now available methods of treating Parkinson's disease or other diseases, in a human or other mammal, by administering an effective amount of an MAO A inhibitor by an intranasal, intrapulmonary, or parenteral route. Parenteral routes of administration include subcutaneous, transdermal, intradermal, intravenous, intramuscular, intraperitoneal, topical, rectal, or vaginal routes, or via an implanted reservoir. Reversible or irreversible MAO A inhibitors can be used; furthermore, more than one MAO A inhibitor can be administered concurrently. The MAO A inhibitor can be selective for MAO A or non-selective (i.e., inhibiting both MAO A and MAO B). The MAO A inhibitor can be administered in conjunction with other drugs, such as MAO B inhibitors. The current invention minimizes the peripheral side effects of MAO A inhibitors, particularly the "cheese effect", by maintaining significant MAO A activity in the intestine. Thus, the use of MAO A inhibitors for the treatment of Parkinson's disease is now possible. Furthermore, MAO A inhibitors can now be used, with minimal side effects, for any other disease or condition for which MAO A inhibitors are therapeutically beneficial.

DETAILED DESCRIPTION OF THE INVENTION

Figure 1:
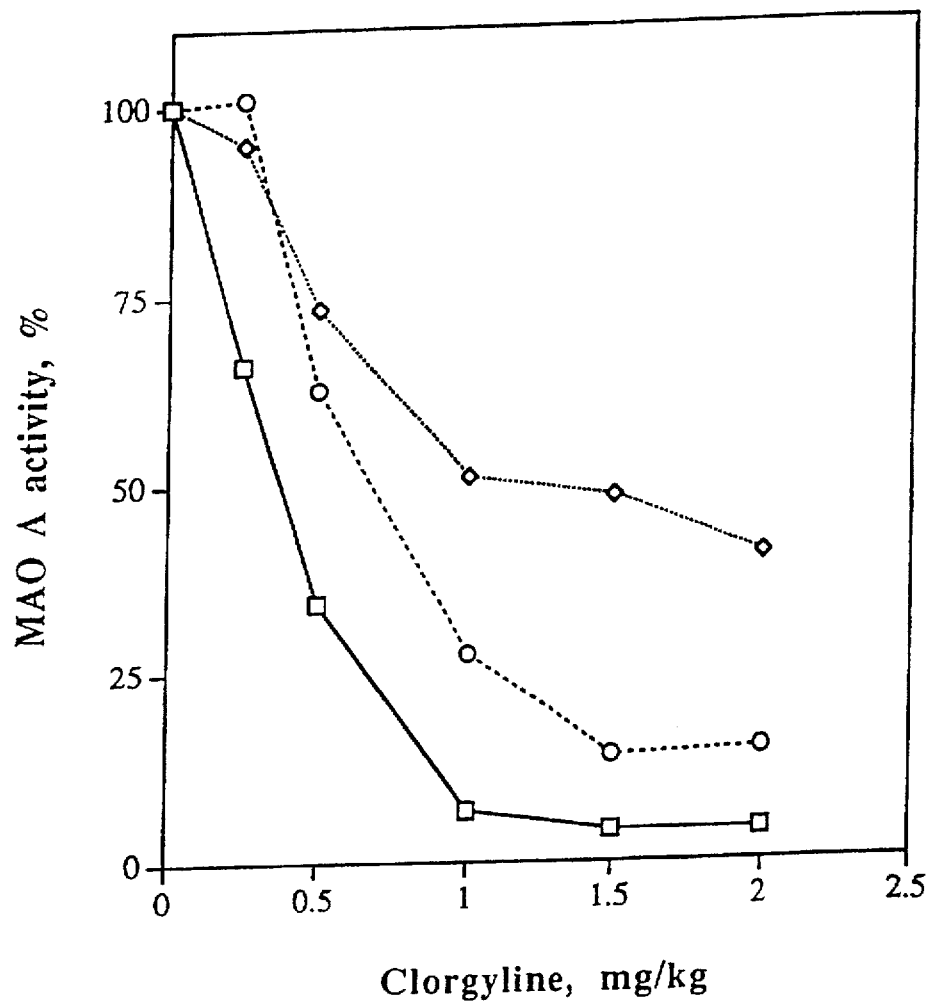
FIG. 1 is a graphic representation of the level of MAO A activity (percent) in mouse striatum, liver, and intestine, five hours after parenteral administration of varying dosage levels of clorgyline (mg/kg). Squares, striatum; diamonds, liver; circles, intestine.

The current invention concerns the discovery that parenteral delivery of an MAO A inhibitor at a relatively low dose can be used to inhibit MAO A in the nigrostriatal system, while minimizing MAO A inhibition in the gut and liver. As described in the Examples below, Applicant has discovered that subcutaneous administration of an MAO A inhibitor, clorgyline, differentially blocked MAO A activity in the striatum, while maintaining significant partial MAO A activity in the gut, after either a single dose or repeated doses of the MAO A inhibitor.

As a result of this discovery, methods of treating mammals, and particularly human patients, afflicted with Parkinson's disease, or with other diseases, disorders and conditions in which MAO A inhibitors can have a therapeutic effect, are now available. The methods include administering parenterally to the individual at least one MAO A inhibitor. The term, "individual", refers to the individual mammal; representative mammals include bovine, ovine, equine, canine, and feline mammals, as well as human. The term, "MAO A inhibitor", as used herein, refers to reversible as well as irreversible MAO A inhibitors. The MAO A inhibitors can be selective for MAO A (e.g., altering MAO A activity while not significantly altering MAO B activity), or non-selective (altering both MAO A and MAO B activity). The term "MAO A inhibitor", as used herein, thus includes both inhibitors that are selective for MAO A, and also inhibitors that are non-selective and affect both MAO A and MAO B activity. It is also understood that, although the term, "MAO A inhibitor" is singular, more than one MAO A inhibitor can be used concurrently in the methods of the invention.

Examples of selective MAO A inhibitors include clorgyline (May & Baker); cimoxatone (MD780515, MD-770222) (Synthelabo); befloxatone (MD-370503) (Synthelabo); brofaromine (Consonar, CGP-11305A) (Ciba-Geigy); bazinaprine (SR 95191) (Sanofi); BW-616U (Burroughs Wellcome); BW-1370U87 (Burroughs Wellcome); CS-722 (RS-722) (Sankyo); E-2011 (Eisai); harmine; harmaline; moclobemide (Aurorix, RO 11-1163) (Roche); PharmaProjects 3975 (Hoechst); RO 41-1049 (Roche); RS-8359 (Sankyo); T-794 (Tanabe Seiyaku); toloxatone (Humoryl, Perenum, MD-690276, MD-69276) (Synthelabo); K-Y 1349 (Kalir and Youdim); LY-51641 (Lilly); LY-121768 (Lilly); M&B 9303 (May & Baker); MDL 72394 (Marion Merrell); MDL 72392 (Marion Merrell); sercloremine (CGP-4718A) (Ciba-Geigy); and MO 1671.

Examples of non-selective MAO inhibitors include amiflamine (FLA-336, FLA-668, FLA-788) (Astra); vanoxerine (boxeprazine) (Novo-Nordisk); AGN 2253 (Nicholas Kiwi); iproniazid (Marsilid); isocarboxazid (Marplan) (Roche); M-3-PPC (Draxis); nialamid (Niamid); phenelzine (Nardil) (Parke-Davis); pargyline (Euronyl) (Abbott); and tranylcypromine (Parnate) (Smith-Kline Beecham).

Other MAO A inhibitors which can be used include budipine (BY-701) (Byk Gulden); caroxazone (Timostenil, FI-6654) (Pharmacia Upjohn, Farmitalia); D-1711 (Biocodex); fezolamine (WIN-41528-2) (Sanofi); FLA-334 (RAN-113) (Astra); FLA-289 (FLA-299, FLA-365, FLA-384, FLA-463, FLA-727) (Astra); K-11566 (Pharmacia Upjohn, Farmitalia); K-11829 (Pharmacia Upjohn, Farmitalia); metralindole; MPCPAM (Yissum); PharmaProjects 227 (Syntex/Roche); PharmaProjects 2806 (Fournier); PharmaProjects 1122; PharmaProjects 3311 (Roche); PharmaProjects 4433 (Roche); RS-2232 (Sankyo); and UP-614-04 (Bristol-Myers).

The MAO A inhibitor (or inhibitors) is administered nasally, via an intrapulmonary route (intrapulmonarily), or parenterally (i.e., by any means other than through the gastrointestinal tract or lungs). For example, the MAO A inhibitor can be administered subcutaneously, transdermally, intradermally, intravenously, intramuscularly, intraperitoneally, topically, rectally, vaginally, or via an implanted reservoir. In a preferred embodiment, the MAO A inhibitor is administered intradermally or transdermally. The term "transdermal" includes passive transdermal and also electrotransdermal (e.g., iontophoretic or electroosmotic) delivery. Representative intradermal delivery means are described in U.S. Pat. Nos. 5,279,544 and 5,527,288; and in U.S. patent application Ser. Nos. 08/647,954, 08/532,707, 60/003,673, 60/008,499, 60/019,714. Representative transdermal delivery means are described in U.S. Pat. Nos. 5,156,591; 5,533,995; 4,592,753; 4,822,617; 5,062,834; 5,425,706; 5,090,963; 5,242,406; 5,246,147; and 5,186,805; U.S. patent application Ser. No. 08/591,583; and PCT/IE95/00031. Representative electrotransdermal and other transdermal delivery means are described in U.S. Pat. Nos. 4,557,723; 4,640,689; 5,135,497; 4,883,457; 5,358,483; 5,328,453; 5,356,632; 4,662,031; 4,919,648; 5,224,928; 4,856,188; 4,734,090; 5,135,478; 5,380,272; 4,713,050; 4,921,475; 4,808,152; 4,865,582; 5,163,899; 5,328,452; 4,708,716; 5,087,240; 4,731,926; 5,167,617; 5,088,977; and 5,135,480. The entire teachings of each of the above-named patents and patent applications are incorporated herein in their entirety.

The MAO A inhibitor can be administered in dosage formulations containing conventional, non-toxic, physiologically-acceptable carriers, adjuvants, and/or vehicles. The formulation in which the MAO A inhibitor is administered will depend at least in part on the route by which it is administered. Other agents, such as MAO B inhibitors (e.g., selegiline (deprenyl)), levodopa, decarboxylase inhibitors, dopamine agonists, anticholinergics, COMT inhibitors, antioxidants, antidepressants, NMDA antagonists, neutrotrophic factors, or other anti-Parkinsonian drugs, can also be administered in conjunction with the MAO A inhibitor.

The MAO A inhibitor is administered in an effective amount, which is that amount necessary to alleviate, reduce, or eliminate the symptoms associated with the disease, disorder or condition to be treated or to slow disease progression. The MAO A inhibitor can also be administered prophylactically, in order to prevent symptoms associated with the disease, or to delay onset of symptoms associated with the disease. If more than one MAO A inhibitor is used, the effective amount is that amount of the combination of MAO A inhibitors that is necessary to alleviate, reduce, eliminate, prevent, or delay onset of the symptoms associated with disease, disorder or condition or to slow disease progression. The effective amount will be determined on an individual basis, and will be based in part, on consideration of the particular MAO inhibitor, the individual's size and gender, the severity of the symptoms to be treated, the result sought, and the disease, disorder or condition to be treated or prevented. The effective amount will generally be an amount which decreases striatal MAO A activity by at least about 15%, and preferably at least about 30%, and more preferably at least about 50%, and even more preferably at least 70%, while maintaining at least about 15%, and preferably at least about 30%, of the MAO A activity in the intestines. Usually, the effective amount will be between approximately 0.001 mg/kg to 1 g/kg, preferably about 0.01 mg/kg to 10 mg/kg. For example, it was found that if the MAO A inhibitor is clorgyline, the preferred effective amount in mice to inhibit 90% of striatal MAO A while maintaining 50% of intestinal MAO A activity is 0.6 mg/kg. One of ordinary skill in the art is able to extrapolate the preferred effective amount in a human. The effective amount can be determined by one of ordinary skill in the art, employing such factors and using no more than routine experimentation.

The effective amount can be administered in a series of doses separated by appropriate intervals, such as hours, days, or weeks. Alternatively, the effective amount can be administered as a sustained release dose, such as by a controlled-release dosage formulation.

Representative diseases, disorders and conditions in which MAO A inhibitors could have a therapeutic effect include: Parkinson's disease (either idiopathic or familial), parkinsonism, depression (including depression refractory to tricyclic antidepressants, selective serotonin reuptake inhibitors, or orally-administered MAO inhibitors), Alzheimer's disease, Huntington's disease, dementia, neurodegenerative diseases, attention deficit disorder, migraine, narcolepsy, psychiatric disorders, panic disorders, social phobias, anxiety, psychoses, obsessive-compulsive disorders, obesity or eating disorders, body dysmorphic disorders, post-traumatic stress disorders, conditions associated with aggression, drug abuse treatment, or smoking secession. The MAO A inhibitor can be administered not only to treat symptoms of these diseases, disorders and conditions, but also to delay of prevent or delay onset or worsening of symptoms of these diseases, disorders and conditions. For example, it has been suggested that MAO inhibitors can serve as neuroprotective agents in Parkinson's disease. Because Parkinson's disease is caused by premature death of nerve cells in the substantia nigra of the brain, use of MAO inhibitors can reduce or eliminate premature cell death, and thereby prevent or slow down the onset of symptoms of disease. Neuroprotection can thus be significantly valuable in the treatment of Parkinson's disease, as well as other neurodegenerative diseases which are caused by the death or dysfunction of cells in the central nervous system.

The invention is further and more specifically illustrated by the following Examples.

EXAMPLE 1

Inhibition of MAO A Activity in the Brain, and Maintenance of Activity in Gut of Mice The purpose of these experiments was (i) to demonstrate that substantial inhibition of MAO A could be achieved in the brain while maintaining significant enzyme activity in the gut, and (ii) to establish the lowest dose of the MAO A inhibitor clorgyline able to accomplish this goal when administered subcutaneously.

All experiments were performed in strict accordance with the National Institutes of Health (NIH) Guide for the Care and Use of Laboratory Animals. C57BL/6 mice were housed under constant temperature (22° C.) and humidity conditions in a room illuminated for 12 hours per day, with food and water freely available. Mice (n=5/group) were administered subcutaneously the MAO A inhibitor, clorgyline, at one of the following doses: 0; 0.25; 0.5, 0.6; 0.8; 1.0; or 2.0 mg/kg. Animals were sacrificed five hours after drug administration. Brains were removed, and dissection of the striata was performed within two minutes of cervical dislocation. Tissues were collected in buffer (pH 7.2), sonicated for approximately 10 seconds, and stored at −70° C. Similar procedures were used to collect, homogenize and store samples from the liver and gut of the animals.

MAO A and MAO B activity were measured as previously described (Yu and Hertz, *J. Neurochem.* 39:1492–5 (1982)), using 14C-phenylethylamine and 14C-5-hydroxytryptamine as selective substrates for MAO B and MAO A, respectively. Preliminary experiments were performed to ensure that enzyme activity was linear with respect to time and enzyme concentration, and that no more than 10–20% of the substrate was consumed during the incubation period (data not shown). Protein was measured by the method of Lowry et al. (*J. Biol. Chem.* 193:265–75 (1951)).

Figure 2:
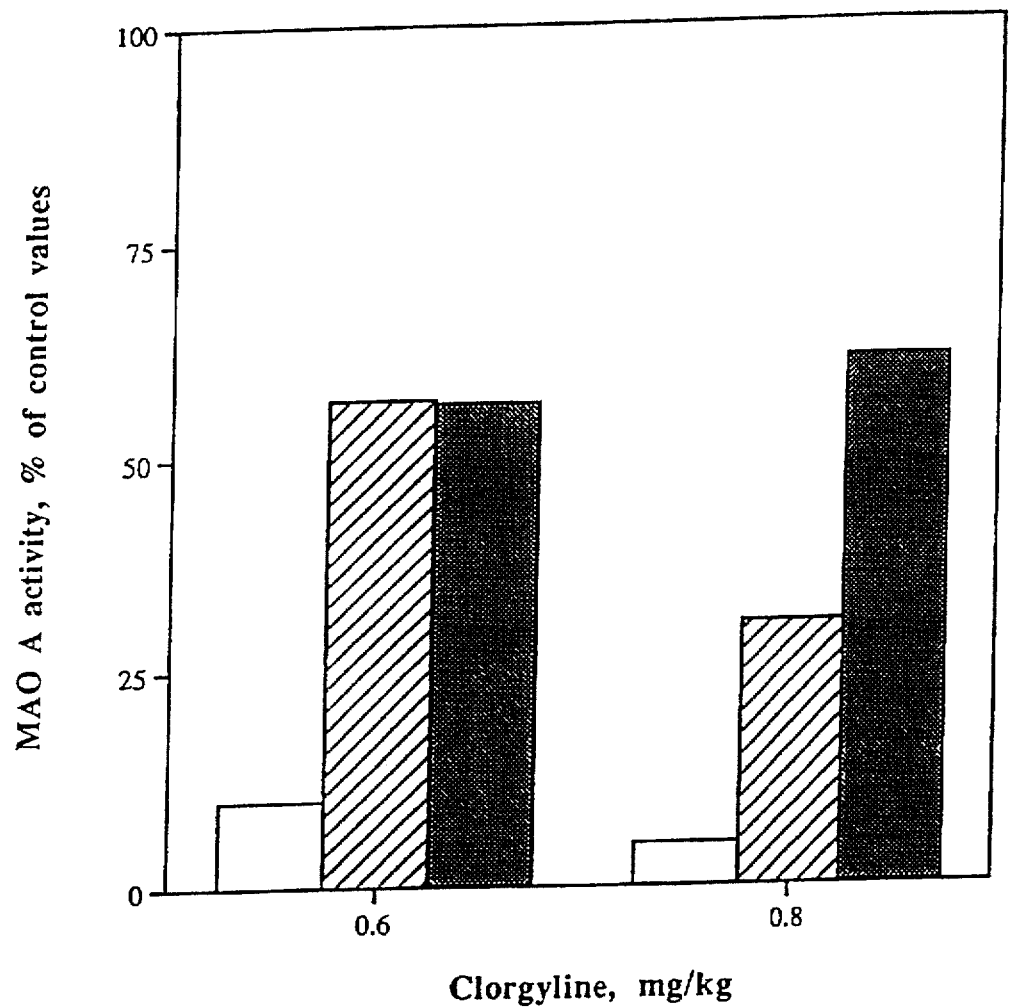
FIG. 2 is a graphic representation of the level of MAO A activity (percent of control) in mouse striatum, liver, and intestine, five hours after parenteral administration of two different dosage levels of clorgyline (0.6 or 0.8 mg/kg). Open bars, striatum; hatched bars, intestine; filled bars, liver.

Results indicated that the curve of MAO A inhibition was steeper in the striatum as compared to both the liver and the gut (FIG. 1). With 1 mg/kg clorgyline, >90% inhibition was achieved in the striatum while MAO activity was still 51% and 27% of control in the liver and gut, respectively. With 0.6 mg/kg clorgyline, 90% inhibition of MAO A activity was measured in the striatum as compared to >50% activity remaining in the liver or the gut. With 0.8 mg/kg, activity in the liver was still about 50%, but it was reduced to 31% in the gut (FIG. 2).

Figure 3:
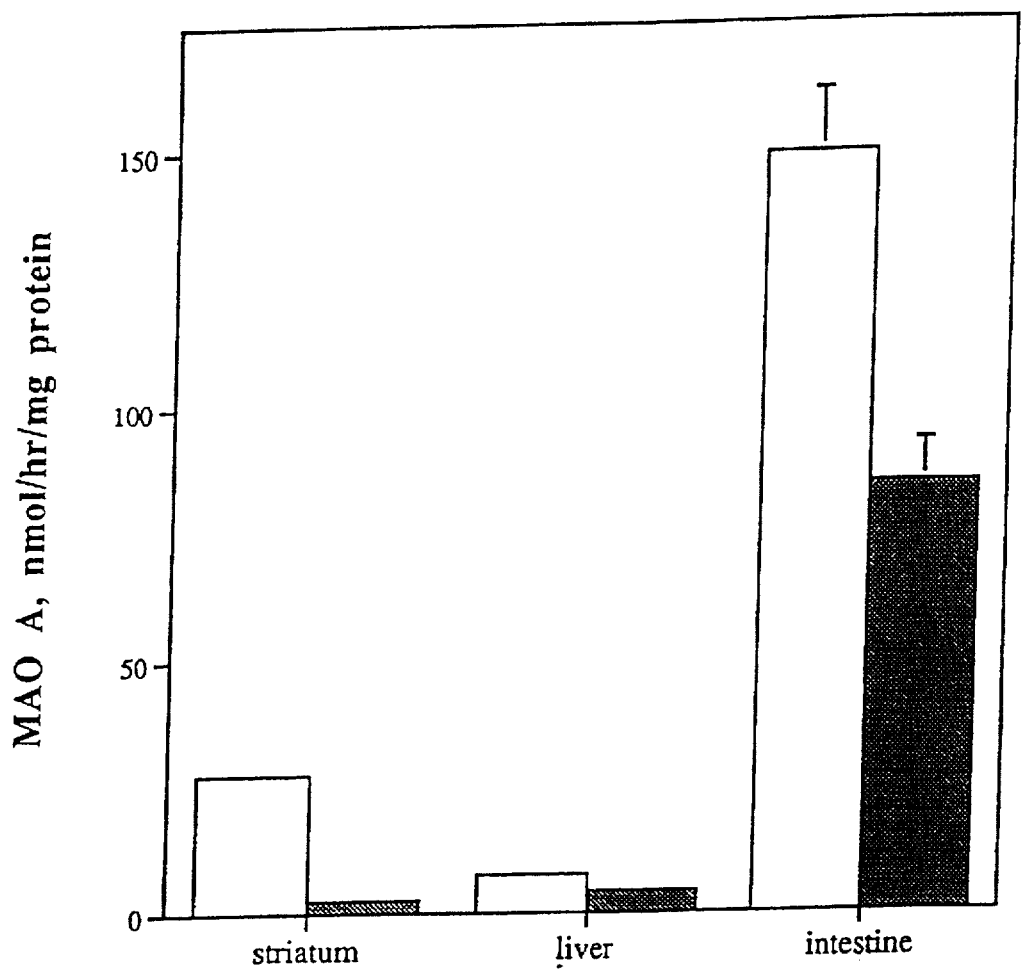
FIG. 3 is a graphic representation of the actual values (nmol/hour/mg protein) for MAO A activity in mouse striatum, liver, and intestine, five hours after parenteral administration of clorgyline or saline (control). Open bars, saline; filled bars, clorgyline (0.6 mg/kg).

A comparison of MAO A activity in clorgyline-treated (0.6 mg/kg) compared with untreated mice clearly shows that MAO A activity in the gut is substantially higher than in the striatum or the liver, when activity is expressed as actual values (nmol/hour/mg protein) rather than as percent (FIG. 3). Furthermore, even after clorgyline treatment, MAO A activity in the gut is approximately three times greater than the basal striatal MAO activity in untreated animals.

Figure 4:
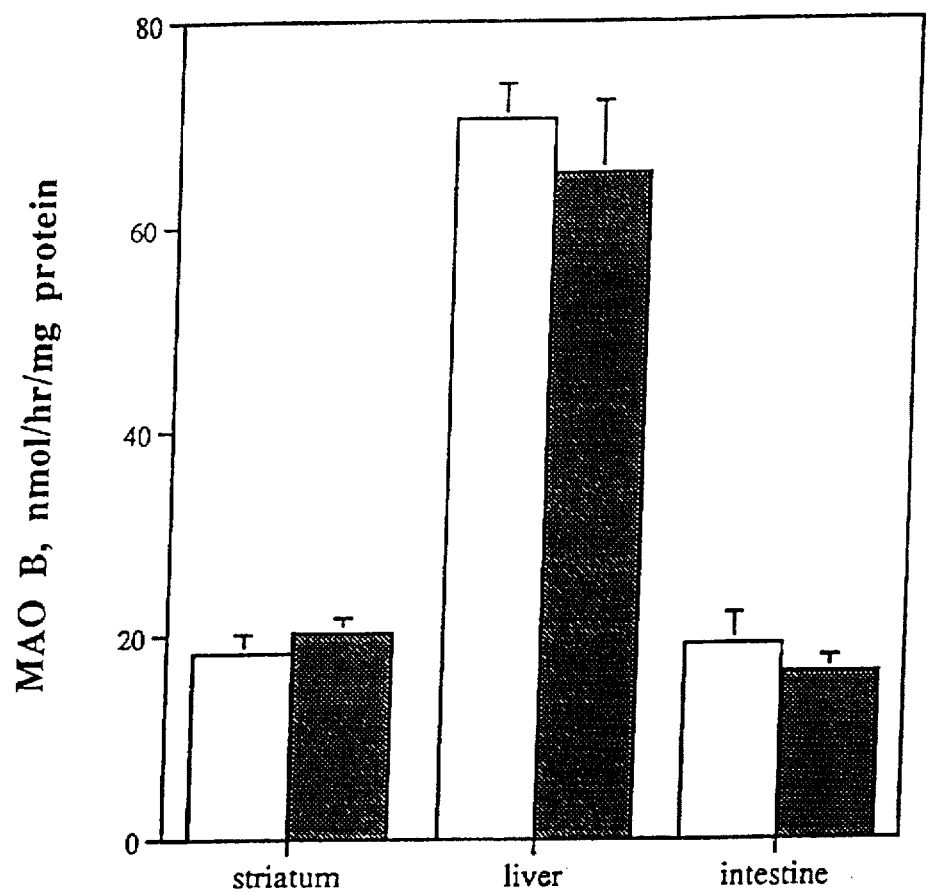
FIG. 4 is a graphic representation of the actual values (nmol/hour/mg protein) of MAO B activity in mouse striatum, liver, and intestine, five hours after parenteral administration of clorgyline or saline (control). Open bars, saline; filled bars, clorgyline (1.0 mg/kg).

Doses of clorgyline used in these experiment selectively inhibit MAO A. No difference in MAO B activity was observed in mice injected with 1 mg/kg clorgyline as compared to mice injected with saline (FIG. 4). Furthermore, as shown in Table 1, below, no significant differences in MAO A activity were found in the striatum, liver or gut, when comparing MAO activity in young (7–8 week-old) and old (15 month-old) mice.

TABLE 1

Comparison of MAO A Activity in Young vs. Old Mice

| | MAO A (nmol/hr/mg protein) | | |
|---|---|---|---|
| | Striatum | Liver | Intestine (Gut) |
| Young mice | 27.9 ± 0.5 | 8.0 ± 0.4 | 149.2 ± 12.5 |
| Old mice | 20.1 ± 0.8 | 11.3 ± 1.0 | 162.0 ± 6.2 |

These experiments demonstrated that parenteral administration of an MAO A inhibitor blocks differentially the enzyme in the brain, as compared with the liver and gut, without affecting MAO B activity. Because MAO A activity in the gut is very high, it can be extrapolated that partial enzyme inhibition will avoid drug side effects due to ingestion of foods. The effects of MAO A inhibitors were unlikely to vary depending on age, since MAO A activity was similar in the striatum, liver and gut in both young and old animals.

EXAMPLE 2

Comparison of Parenteral and Oral Administration of MAO A Inhibitors

To simulate chronic administration, experiments were performed to compare the effects of parenteral and oral administration of two doses of MAO A inhibitors identified by the experiments described in Example 1. The dose of clorgyline used in these experiments was chosen based on the data, described in Example 1, indicating that 0.6 mg/kg clorgyline causes approximately 50% MAO A inhibition in the gut and liver, while >90% inhibition in the mouse striatum.

Mice were divided into four groups (n>10/group, in 2-3 different sets of experiments) and treated with saline or 0.6 mg/kg clorgyline either subcutaneously (s.c.) or via oral gavage. Five hours after clorgyline/saline administration, mice were killed by cervical dislocation and MAO A activity was measured in the striatum, gut and liver, as described in Example 1.

Figure 5:
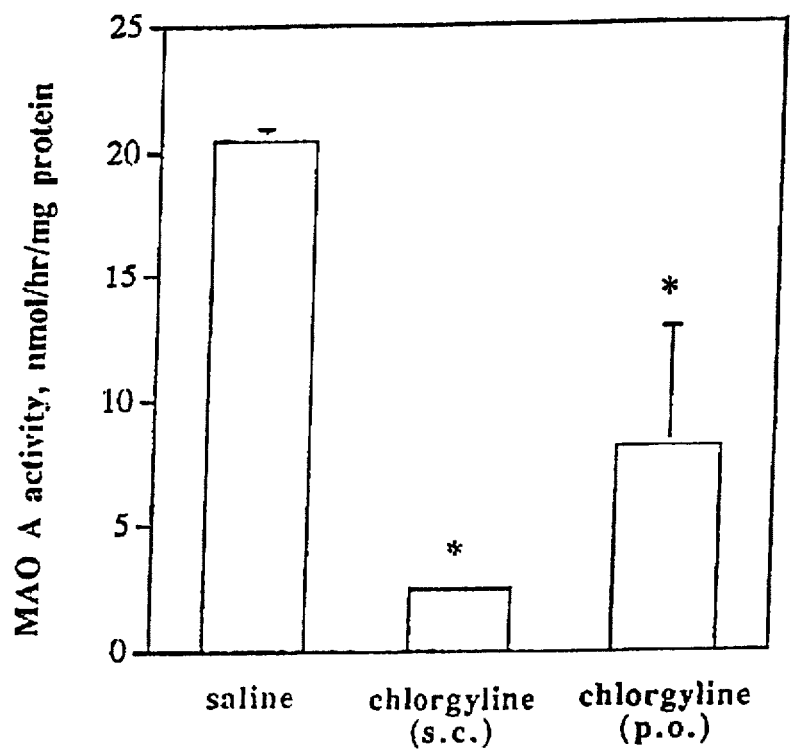
FIG. 5 is a graphic representation of actual values (nmol/hour/mg protein) for MAO A activity in mouse striatum, five hours after administration of saline (control), subcutaneously (s.c.) administered clorgyline, or orally (p.o.) administered clorgyline. Asterisk (*) indicates statistical difference ($p<0.005$) from control.

MAO A activity was not different in control animals treated with saline subcutaneously or orally. Both parenteral and oral administration of clorgyline significantly inhibited MAO activity in the striatum to 11% (parenteral) and 40% (oral) of control values, as shown in FIG. 5. There was great variability in the extent of striatal MAO A inhibition with oral clorgyline (as reflected by the high SEM of the value) while inhibition with subcutaneous clorgyline was consistently about 90%. The variability with oral clorgyline was observed in three different sets of experiments, ruling out the possibility of dosing errors, and suggesting that it may be related to different degrees of drug absorption in individual animals. Because of the variability, the difference between clorgyline inhibition induced by subcutaneous vs. oral administration did not reach statistical significance at the 0.05 significance level. The more consistent MAO A inhibition achieved by subcutaneous delivery is an additional benefit of parenteral delivery over oral delivery.

Figure 6:
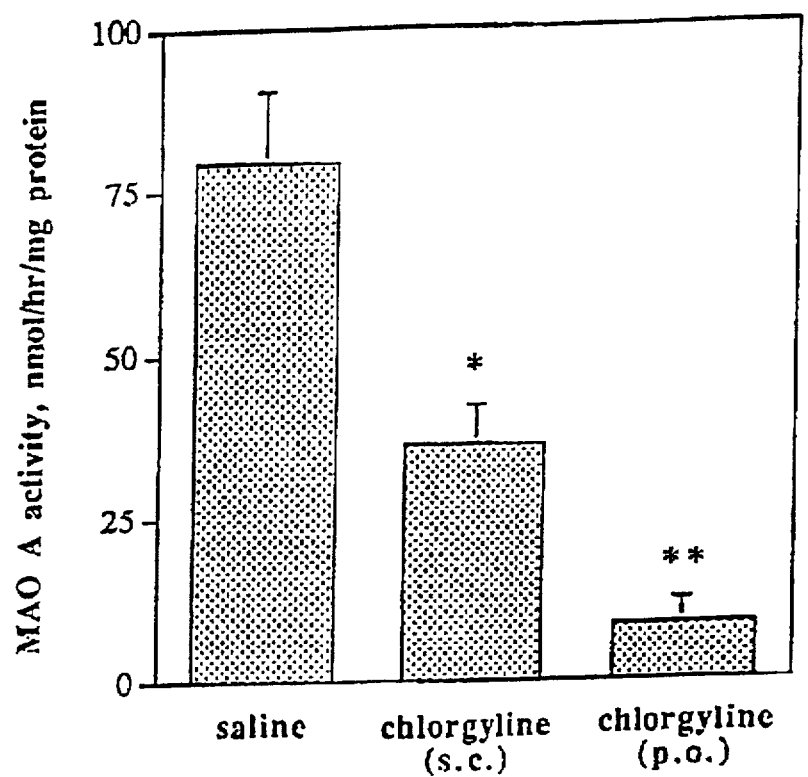
FIG. 6 is a graphic representation of actual values (nmol/hour/mg protein) for MAO A activity in mouse intestine, five hours after administration of saline (control), subcutaneously (s.c.) administered clorgyline, or orally (p.o.) administered clorgyline. Asterisk (*) indicates statistical difference from control ($p<0.003$). Double asterisk (**) indicates statistical difference from control ($p=0.0001$) and from clorgyline s.c. ($p<0.04$).

The effects of subcutaneous and oral clorgyline administration on intestinal MAO A activity is shown in FIG. 6. Both parenteral and oral administration significantly inhibited MAO A activity. However, the extent of inhibition was significantly greater when clorgyline was given orally (89%) as compared to parenterally (55%). Indeed, in the latter case, relatively high MAO A activity (approximately 30 nmol/hr/mg protein) was still present in the gut of clorgyline-treated mice.

Figure 7:
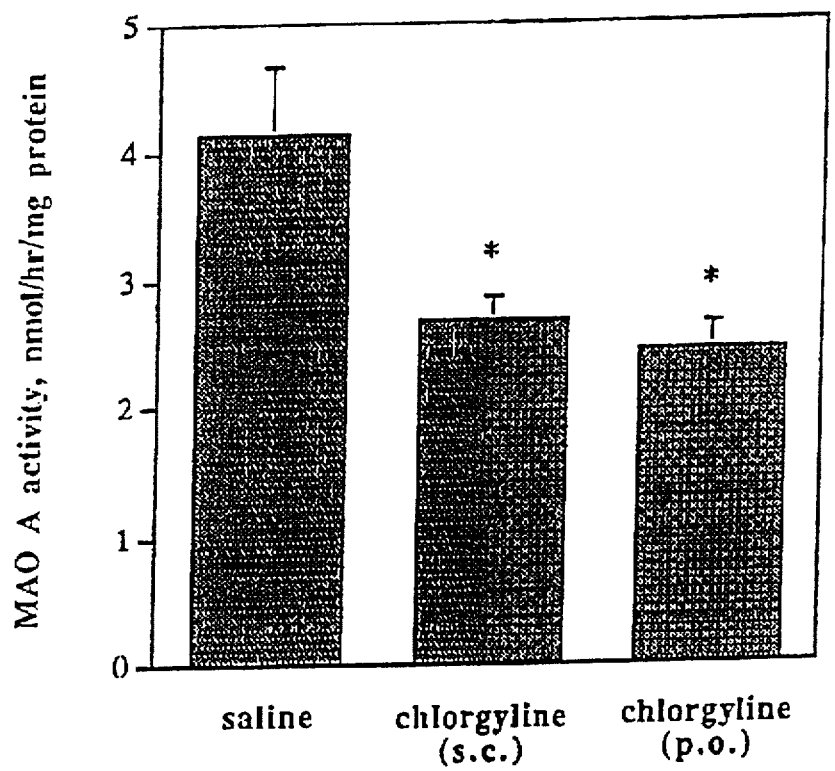
FIG. 7 is a graphic representation of actual values (nmol/hour/mg protein) for MAO A activity in mouse liver, five hours after administration of saline (control), subcutaneously (s.c.) administered clorgyline, or orally (p.o.) administered clorgyline. Asterisk (*) indicates statistical difference ($p<0.02$) from control.

No significant difference was measured in the extent of inhibition of MAO A activity caused by oral, as compared with subcutaneous, clorgyline treatment in the liver (FIG. 7).

These experiments demonstrated that parenteral injection exerts a more consistent and potent inhibitory effect in the brain, whereas oral administration results in a significantly more pronounced MAO inhibition in the gut than in the brain. Furthermore, parenteral injection, but not oral administration, is able to block 90% of MAO A activity in the brain while maintaining 50% activity in the gut. In absolute values, this residual 50% intestinal activity (>40 nmol/hr/mg protein) is greater than the 100% activity in striatum (20 nmol/hr/mg protein) or liver (4 nmol/hr/mg protein). The extent of inhibition achieved by 0.6 mg/kg clorgyline in the liver is not affected by its route of administration, as more than 50% MAO A activity is consistently present in the liver after clorgyline exposure.

Thus, with oral administration, almost complete inhibition of MAO A in the gut is necessary before achieving significant inhibition in the brain. In contrast, parenteral administration of these drugs (at specific doses) is able to induce almost complete block of the enzyme in the brain, while maintaining significant activity in the gut.

EXAMPLE 3

Effect of Repeated Administration of MAO A Inhibitors

Experiments were performed to determine whether repeated administration of an irreversible MAO A inhibitor affects the differential levels of inhibition in the different tissues.

Mice (n=5/group) were administered clorgyline at a dose of 0.6 mg/kg either subcutaneously or orally. Mice were killed five hours after a single administration of clorgyline, or five hours after the last of five consecutive treatments given every 24 hours. MAO A activity was measured and compared in the striatum, intestine and liver.

Figure 8:
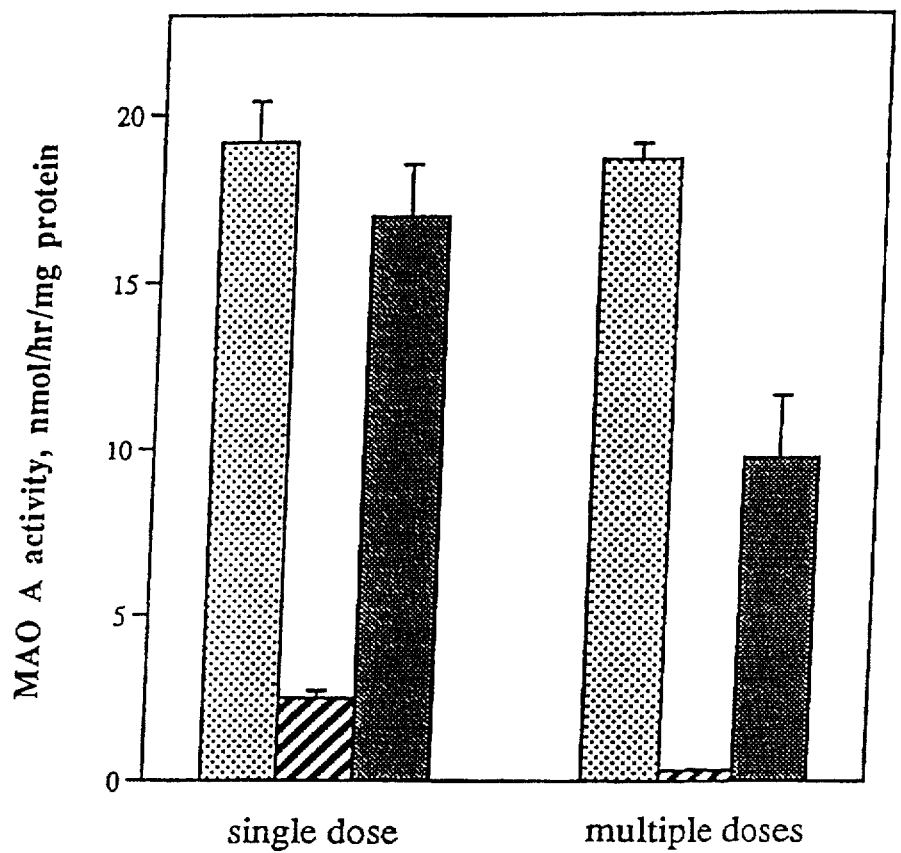
FIG. 8 is a graphic representation of actual values (nmol/hour/mg protein) for MAO A activity in mouse striatum for single or multiple administrations of saline (control), subcutaneously (s.c.) administered clorgyline, or orally (p.o.) administered clorgyline, five hours after the sole or last dose. Dotted bars, saline (control); hatched bars, subcutaneous (s.c.) administration; filled bars, orally (p.o.) administration.

A single administration of clorgyline caused approximately 90% striatal MAO A inhibition when injected subcutaneously, but only 15% inhibition when given orally, as shown in FIG. 8. Repeated subcutaneous injections further reduced striatal MAO A activity to only 2% of the control value. Striatal MAO A was also further inhibited by multiple, as compared to single, administration of clorgyline per os; residual activity was about 50% of control after multiple treatments.

Figure 9:
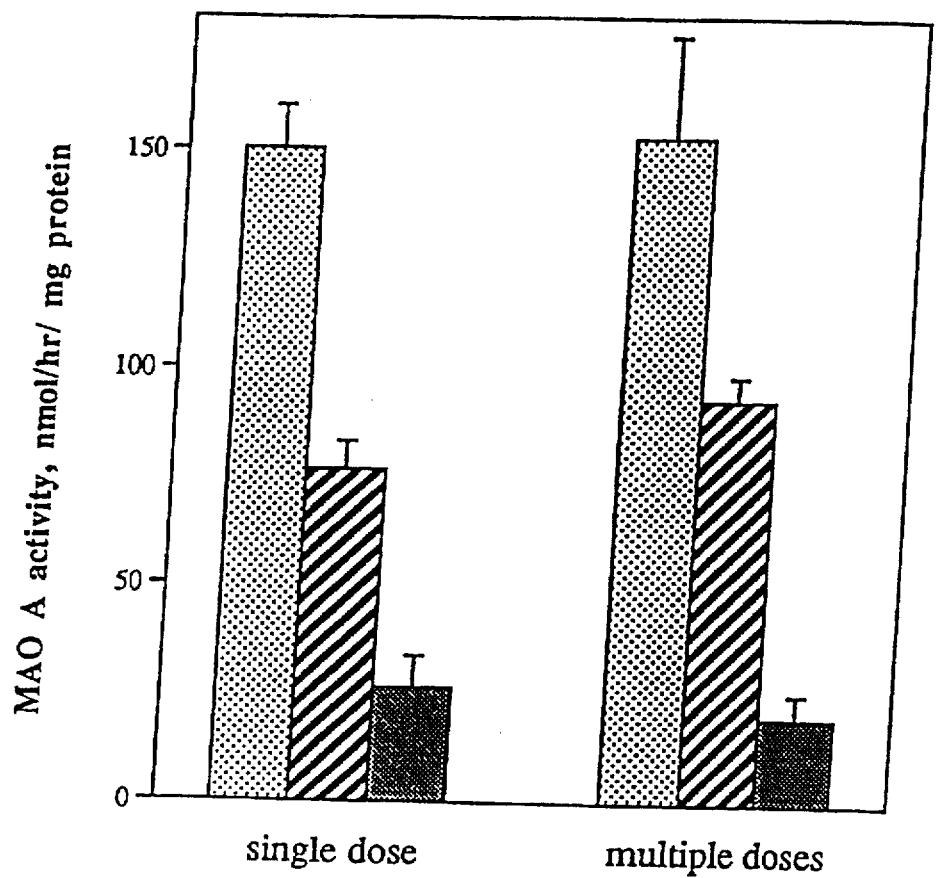
FIG. 9 is a graphic representation of actual values (nmol/hour/mg protein) for MAO A activity in mouse intestine for single or multiple administrations of saline (control), subcutaneously (s.c.) administered clorgyline, or orally (p.o.) administered clorgyline, five hours after the sole or last dose. Dotted bars, saline (control); hatched bars, subcutaneous (s.c.) administration; filled bars, orally (p.o.) administration.

In the intestine (FIG. 9), oral administration of clorgyline was significantly more effective than the subcutaneous injection in inhibiting MAO A. Approximately 20% and 15% of control activity was measured after single and multiple oral administration, respectively. In contrast, the subcutaneous treatment only inhibited 50% of intestinal MAO A, regardless of whether clorgyline was injected once, or for five consecutive days.

Figure 10:
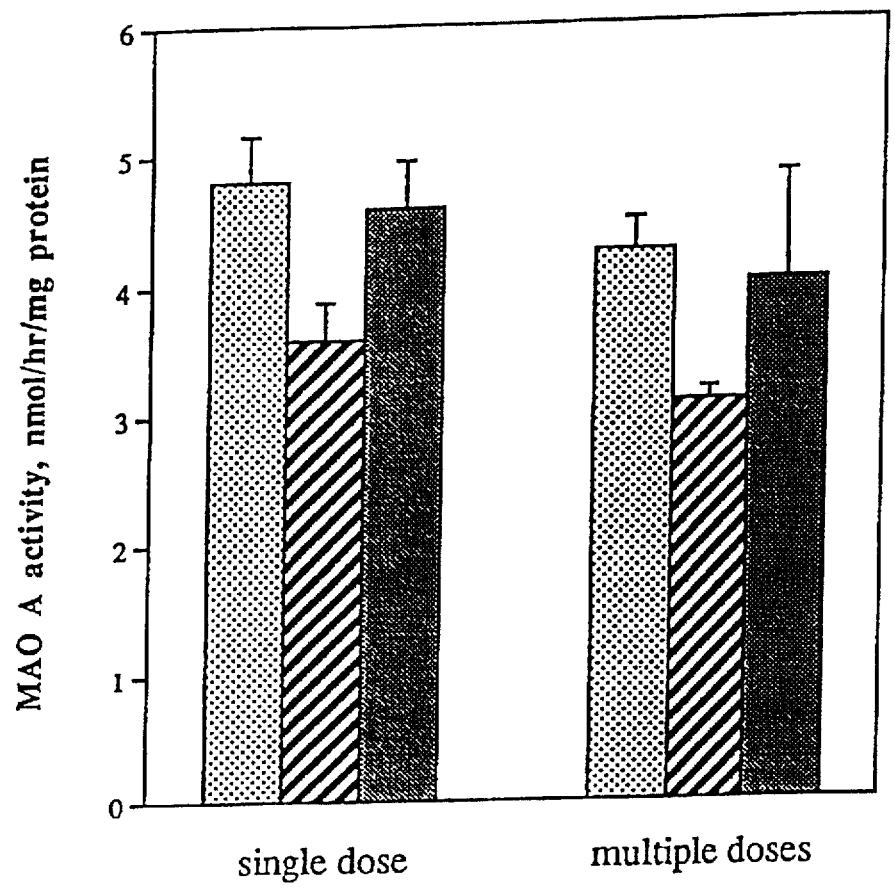
FIG. 10 is a graphic representation of actual values (nmol/hour/mg protein) for MAO A activity in mouse liver for single or multiple administrations of saline (control), subcutaneously (s.c.) administered clorgyline, or orally (p.o.) administered clorgyline, five hours after the sole or last dose. Dotted bars, saline (control); hatched bars, subcutaneous (s.c.) administration; filled bars, orally (p.o.) administration.

MAO A inhibition was never greater than 25% in the liver with either the subcutaneous or oral administration of clorgyline (FIG. 10). Also, no significant changes were seen in the extent of MAO inhibition after single and multiple treatments.

These experiments demonstrated that repeated subcutaneous administration of clorgyline enhanced its effectiveness in inhibiting striatal MAO A, and that oral treatment, even after multiple administrations of clorgyline, is significantly less effective than subcutaneous injection(s) in inhibiting MAO A. Further, multiple subcutaneous treatments with clorgyline do not inhibit more than 50% MAO A activity in the intestine, whereas oral treatment causes a greater MAO A inhibition in the intestine than in the striatum. Hepatic MAO A seemed to be relatively less affected by 0.6 mg/kg clorgyline than striatal or intestinal MAO A activity, regardless of the route or frequency of administration.

In the mouse model, parenteral administration of an irreversible MAO A inhibitor is very effective in inhibiting the enzyme in the central nervous system (CNS), and relatively low doses of the inhibitors can spare significant levels of MAO A in the intestine, even after repeated administration. Therefore, it can be inferred that parenteral administration of MAO A inhibitors in humans can be used to treat Parkinson's disease symptoms, as well as symptoms of other diseases in which MAO inhibitors can have a beneficial effect, while avoiding side effects, such as the "cheese effect," that are associated with inhibition of MAO A activity in the intestine.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of treating Parkinson's disease in a human, comprising administering to the human an effective amount of an irreversible monoamine oxidase A inhibitor selected from the group consisting of nonheterocyclic compounds comprising either an amine or hydrazine functionality, by a route selected from the group consisting of:

parenteral, intranasal and intrapulmonary.

2. The method of claim 1, wherein the monoamine oxidase A inhibitor is administered parenterally by a route selected from the group consisting of: subcutaneous, transdermal, intradermal, intravenous, intramuscular, intraperitoneal, topical, vaginal and via an implanted reservoir.

3. The method of claim 2, wherein the monoamine oxidase A inhibitor is administered subcutaneously.

4. The method of claim 2, wherein the monoamine oxidase A inhibitor is administered transdermally.

5. The method of claim 2, wherein the monoamine oxidase A inhibitor is administered intradermally.

6. The method of claim 1, wherein the monoamine oxidase A inhibitor is selective for monoamine oxidase A.

7. The method of claim 1, wherein the monoamine oxidase A inhibitor is also an inhibitor of monoamine oxidase B.

8. The method of claim 1, wherein the monoamine oxidase A inhibitor is administered in conjunction with a monoamine oxidase B inhibitor.

9. A method of treating Parkinson's disease in a human, comprising administering to the human an effective amount of more than one irreversible monoamine oxidase A inhibitor, each irreversible monoamine oxidase A inhibitor being selected from the group consisting of nonheterocyclic compounds comprising either an amine or hydrazine functionality, by a route selected from the group consisting of:

parenteral, intranasal and intrapulmonary.

10. A method of treating Parkinson's disease in a human, comprising administering to the human an amount of at least one irreversible monoamine oxidase A inhibitor selected from the group consisting of nonheterocyclic compounds comprising either an amine or hydrazine functionality, the amount being sufficient to reduce striatal monoamine oxidase A activity by at least about 30%, while maintaining at least about 15% of intestinal monoamine oxidase A activity, by a route selected from the group consisting of:

parenteral, intranasal, and intrapulmonary.

11. The method of claim 10, wherein striatal monoamine oxidase A activity is reduced by about 50%.

12. The method of claim 11 wherein at least about 30% of intestinal monoamine oxidase A activity is maintained.

13. A method of treating Parkinsonism in a human, comprising administering to the human an effective amount of at least one irreversible monoamine oxidase A inhibitor selected from the group consisting of nonheterocyclic compounds comprising either an amine or hydrazine functionality, by a route selected from the group consisting of:

parenteral intranasal and intrapulmonary.

* * * * *